United States Patent [19]

MacFarlane

[11] Patent Number: 5,246,430
[45] Date of Patent: Sep. 21, 1993

[54] REINFORCED CHOLANGIOGRAM CATHETER

[75] Inventor: Richard H. MacFarlane, Geneva, Ill.

[73] Assignee: Taut, Inc., Geneva, Ill.

[21] Appl. No.: 858,942

[22] Filed: Mar. 27, 1992

[51] Int. Cl.$^5$ .................. A61M 25/00; A61B 6/00
[52] U.S. Cl. ................................. 604/282; 128/658
[58] Field of Search ............... 604/52, 53, 264, 280, 604/282, 270, 96; 606/194; 128/656-658

[56] References Cited

U.S. PATENT DOCUMENTS

| | | | |
|---|---|---|---|
| 2,472,483 | 6/1949 | Krippendorf | 604/282 X |
| 3,448,739 | 6/1969 | Stark et al. | 128/658 |
| 3,498,286 | 3/1970 | Polanyi et al. | 604/282 X |
| 3,618,613 | 11/1921 | Schulte | 604/282 X |
| 3,780,740 | 12/1973 | Rhea | 604/270 |
| 3,924,632 | 12/1975 | Cook | 604/282 X |
| 4,030,505 | 6/1977 | Tessler | 128/328 |
| 4,137,906 | 2/1979 | Akiyama et al. | 128/658 |
| 4,306,563 | 12/1981 | Iwatschenko | 604/282 X |
| 4,306,566 | 12/1981 | Sinko | 128/658 |
| 4,484,585 | 11/1984 | Baier | 128/748 |
| 4,719,924 | 1/1988 | Crittenden et al. | 128/772 |
| 4,747,823 | 5/1985 | Buclanan | 604/49 |
| 4,782,834 | 11/1988 | Maguire et al. | 606/194 |
| 5,078,702 | 1/1992 | Pomeranz | 604/280 |
| 5,152,756 | 10/1992 | Quinn et al. | 604/270 |
| 5,156,594 | 10/1992 | Keith | 604/96 |

Primary Examiner—John D. Yasko
Assistant Examiner—Alan J. Celmak
Attorney, Agent, or Firm—Malloy & Malloy

[57] ABSTRACT

A cholangiogram catheter having a distally reinforced headed end zone, the cholangiogram catheter being of a polypropylene tubular length; and the headed end zone has an intermediate zone between the distal end and the main length which is of reduced outside diameter relative to the headed tip and the main length and which is reinforced by a rigid support tube of needlestock.

12 Claims, 1 Drawing Sheet

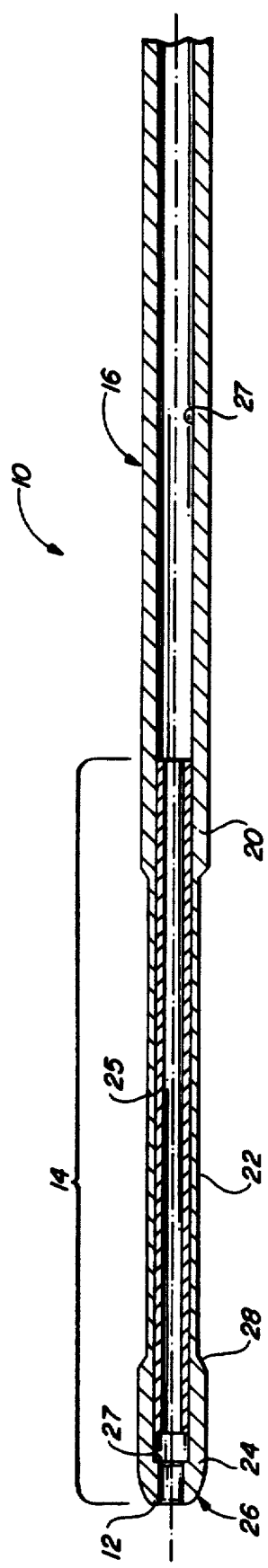

REINFORCED CHOLANGIOGRAM CATHETER

BACKGROUND OF THE INVENTION

In the past, gallbladder operations have been quite common. Such operations were big operations although not especially dangerous. Because such operations were big, the recovery time from such an operation was substantial. In conducting such an operation, an incision was made and, first, through a cholangiogram catheter inserted into the cystic duct, radio opaque material was forced. Thereafter, through x-ray procedures, determination was then made as to whether or not to remove the gallbladder.

Cholangiogram catheters, upon the forcing of radio opaque material into the duct, were known to be forced out of the incision in the duct by the back pressure built up by the radio opaque material. It became common, to avoid this, to provide a cholangiogram catheter with a headed tip. The tip would be inserted about ⅛ into the cystic duct of a patient. Thereafter, the duct was tied about the catheter adjacent the headed tip so that the headed end could not be forced back out by back pressure since a shoulder at the headed end would captivate it against such back pressures when the duct was tied about it. Subsequently, instead of ties, clamps, usually of titanium, were developed which are applied by a device with jaws. The jaws would apply pressure to the clamp which would cause the clamp to close about the cystic duct and catheter within it near its shoulder.

To feed the catheter into an incision in the cystic duct, it is necessary, of course, to push axially on the catheter. Catheters, which are required to be of small diameter, were also required to be of sufficient strength so as not to collapse in response to axial pressures, such as those encountered when one attempts to push a string into a hole. If the catheter were made of a preferred two small a diameter, difficulties were encountered. It could not be guided into position and it could collapse when being clamped.

Recently, conventional gallbladder operations are conducted through apertures in the abdomen to reach the gallbladder. A gallbladder requiring removal, was collapsed, such as one might, on analogy, collapse a balloon by permitting the material to be drawn from it. When a gallbladder is collapsed, it can be removed from a small aperture in the abdomen without the necessity for a big operation. This has resulted in gallbladders being performed after which a patient may return home without being required to stay in the hospital and to endure pain during recovery for an extended period of time. In conducting such an operation, it has become necessary to provide a cholangiogram catheter which can be easily manipulated into an incision in a cystic duct, advanced about ⅛, and which is, preferably, as small in diameter as possible and which can, in spite of being of small diameter, be secured in position by a clamp without collapsing.

OBJECTS OF THE INVENTION

It is an object of this invention to provide a cholangiogram catheter of small, maximum diameter which nevertheless has a headed tip zone and a reinforced zone adjacent the tip zone so that the catheter can a) be advanced with sufficient rigidity and which will not collapse when clamped in position in the cystic duct.

Generally speaking, it is an object of this invention to provide a thin cholangiogram catheter with a headed tip and main length and an intermediate zone between the headed tip and main length which is of reduced diameter and supported to resist collapse upon application of a clamp or being tied yet which is sufficiently rigid at the tip zone to be inserted through an incision in the cystic duct to a depth of about ⅛ and which can be advanced easily.

It is a general object of this invention to provide an improved cholangiogram catheter of the type set forth and described more fully hereinafter which is highly effective in use and which can easily be positioned and secured adjacent an incision and within a cystic duct.

In accordance with these objects and the description set forth more fully herein, the instant invention will now be described on reference to the accompanying drawing in which:

DESCRIPTION OF THE DRAWINGS

The drawing illustrates a distal end zone of a catheter having a headed tip and a reinforced length of reduced diameter adjacent the headed tip.

DESCRIPTION OF THE PREFERRED EMBODIMENT

Referring to the drawing, there is shown the distal end region of a catheter tube generally designed by the numeral 10. It is a thin catheter of plastic material having a distal end 12 and being of any suitable length. From the distal end 12, extending proximally there is a distal end zone 14 and the extending main length of the catheter 16. Preferably, the main length has a outside diameter of between 0.050" and 0.100" at about 0.060". The catheter is provided with a through hole from the distal end 12 to the proximal end, not shown, which defines a flow path of substantially common diameter. The inside diameter is preferably about 0.032".

Referring now to the distal end zone 14, it is seen that it includes a) a proximal zone 20 preferably with a maximum outside diameter about the same as that of the outside diameter of the main length 16, b) an intermediate zone 22 of reduced outside diameter relative to that of the main length 16, and c) a distalmost headed tip zone 24. The tip zone 24 outside diameter is preferably about the same as the outside diameter of the main length 16, but at least greater than the outside diameter of the intermediate zone, and has a portion 26 which converges distally to the distal end 12 about the through flow path 27. It is seen that the headed tip zone 24, at its proximal end defines a shoulder 28 at the juncture of the tip zone 24 and intermediate zone 22. Within the end zone 14, there is a rigid support tube 25, preferably of steel needlestock which preferably extends into the headed tip zone 24 and also into the proximal zone 20. This is for reinforcing the reduced diameter intermediate zone 22 when the device is inserted into a duct and clamped in position. The clamp bears against the shoulder and resists back pressure so that it is not forced out of the duct through a slit in the duct wall by back pressure when radio opaque material is forced into the duct. In the preferred embodiment, the shoulder 28 diverges outwardly from the intermediate zone and distally at an angle of about 45°; and it is rounded at its maximum diameter.

The catheter is preferably of polypropylene material; and, without the support tube 25, since the tube is of relatively small diameter, for example, 0.060", it is hard to feed it. That would be like pushing a string with a tube. It is very flexible but, because of the support tube, it can be manipulated quite readily. Once in position, however, it is strong enough to resist collapsing when a clamp is applied to the intermediate zone.

In a preferred embodiment, the inside diameter of the main length 16 is about 0.032" while the wall thickness is about 0.015", the common limits in outside diameter of the main length being between 0.040" to 0.100". In the intermediate zone of reduced diameter, however, the plastic wall thickness is about 0.005" and the inside diameter because of the support tube is about 0.020", while the outside diameter of the intermediate zone is reduced to about 0.032". Preferably, the support tube is of 21 gauge stainless steel medical needle stock. Preferably the headed tip 24 is of about the same diameter as that of the outside diameter of the main length. At the distal end, the tip is curved with a radius of curvature of about 0.025". The intermediate zone may be necked down according to the following steps. A mandrel is positioned in the distal end zone 14. Heat is applied to the intermediate zone and the tube is parallel so that necking down takes place as the outside diameter is reduced and the inside diameter is defined by the outside diameter of the mandrel. Preferably about ⅛ of length is reduced in outside diameter. The mandrel may be removed when the polypropylene material cools; and the length of needle stock is inserted to reinforce the weakened wall of reduced wall thickness and outside diameter for the purpose of reinforcing this length. Thereafter, the rounded or headed tip zone is formed. In so doing adjacent the end 12, the inside diameter is reduced relative to the inside diameter of the flow path in the main length defining a shoulder 27 so that the wall thickness of the support tube is captivated against moving out of the end, its outside diameter being than the diameter of the hole at the end 12.

What is claimed is:

1. A headed, thin catheter having a distal end, said catheter comprising:
    (a) a bendable, plastic tube having
        a distal end zone, and
        a main length,
        said main length having an outside diameter of between 0.050" and 0.100", and defining
        an inside through flow path of substantially common diameter,
    (b) said distal end zone comprising:
        a proximal zone of substantially the same outside diameter as that of said main length,
        an intermediate zone of reduced outside diameter relative to that of said main length,
        a distal most headed tip zone having a portion converging distally to the distal end and having a proximal portion of a maximum outside diameter about the same as that of said main length, and
        defining a shoulder at the juncture of said tip zone and intermediate zone, and
    (c) substantially inflexible support tube in the distal end zone, said support tube being sufficiently elongate so as to extend completely along said intermediate zone and thereby reinforce said intermediate zone of reduced diameter such that the catheter cannot easily bend or be compressed along any part of said intermediate zone of reduced diameter.

2. The catheter as set forth in claim 1 wherein said support tube is of stainless steel.

3. The catheter as set forth in claim 1 wherein said support tube extends beyond said intermediate zone and within the headed tip and within the proximal zone.

4. The catheter as set forth in claim 1 of polypropylene plastic material.

5. The catheter as set forth in claim 1 wherein said outside diameter of said main length is about 0.9060".

6. The catheter as set forth in claim 1 wherein said distal end zone is of a length of about ⅛.

7. The catheter as set forth in claim 6 wherein said shoulder diverges distally, and outwardly at an angle of about 45° with respect to the axis of said catheter.

8. A headed, thin catheter having an open distal end and said catheter comprising:
    (a) a bendable tube having
        a distal end zone, and
        a man length of plastic material,
        said main length having an outside diameter of between 0.40" and 0.100", and
        an inside through flow path of substantially common diameter,
    (b) said distal end zone comprising,
        a proximal zone with an outside diameter not greater than the outside diameter of said main length,
        an intermediate zone of reduced outside diameter relative to that of said main length, and
        a distalmost headed tip zone, said tip zone having
            a portion converging distally to the open distal end,
            a proximal portion of a maximum outside diameter greater than the outside diameter of said reduced diameter of said intermediate zone, and
            defining a shoulder at the juncture of said tip zone and intermediate zone, said should diverging distally, and outwardly at an angle of about 45° with respect to the axis of said catheter,
    (c) a substantially inflexible support tube in the distal end zone, said support tube being sufficiently elongate so as to extend completely along said intermediate zone and thereby reinforce said intermediate zone of reduced diameter such that the catheter cannot easily bend or be compressed along any part of said intermediate zone of reduced diameter, and
    means captivating said support tube against distal movement within the catheter.

9. The catheter as set forth in claim 8 wherein said support tube is a tube of stainless steel.

10. The catheter as set forth in claim 9 wherein said tube is of 21 gauge stainless steel.

11. The catheter as set forth in claim 8 wherein the maximum outside diameter of said proximal portion is substantially the same as the outside diameter of said main length.

12. The catheter as set forth in claim 8 wherein said distalmost headed tip zone is of rigid tubular material and said intermediate zone comprises a rigid tube extending from said distalmost headed tip zone and into said main length.

* * * * *

UNITED STATES PATENT AND TRADEMARK OFFICE
CERTIFICATE OF CORRECTION

PATENT NO. : 5,246,430
DATED : September 21, 1993
INVENTOR(S) : Richard H. McFarlane It is certified that error appears in the above-indentified patent and that said Letters Patent is hereby corrected as shown below:

On cover page, item [19] and [75], the inventor's name reading "MacFarlane" should read --McFarlane--.

Signed and Sealed this

Fourteenth Day of March, 1995

*Attest:*

BRUCE LEHMAN

*Attesting Officer*       *Commissioner of Patents and Trademarks*